United States Patent [19]

Krespan et al.

[11] 4,384,128
[45] May 17, 1983

[54] PERFLUOROGLYCIDYL ETHERS

[75] Inventors: Carl G. Krespan; Alicia P. King, both of Wilmington, Del.

[73] Assignee: E. I. Du Pont de Nemours and Company, Wilmington, Del.

[21] Appl. No.: 342,717

[22] Filed: Jan. 25, 1982

Related U.S. Application Data

[62] Division of Ser. No. 250,906, Apr. 3, 1981.

[51] Int. Cl.$^3$ .............................. C07D 303/48
[52] U.S. Cl. .................... 549/550; 549/532
[58] Field of Search .................. 549/550, 532

[56] References Cited

U.S. PATENT DOCUMENTS

| | | | |
|---|---|---|---|
| 2,500,388 | 3/1950 | Simons | 260/614 |
| 2,713,593 | 7/1955 | Brice et al. | 260/535 |
| 3,250,808 | 5/1966 | Moore et al. | 260/535 |
| 3,321,532 | 5/1967 | Lorenz | 260/614 |
| 3,322,826 | 5/1967 | Moore | 260/544 |
| 3,358,003 | 12/1967 | Eleutecio et al. | 260/348 |
| 3,419,610 | 12/1968 | Temple | 260/544 |
| 3,660,315 | 5/1972 | Hill et al. | 260/2 A |
| 4,094,911 | 6/1978 | Mitsch et al. | 549/558 |
| 4,127,615 | 11/1978 | Zahir et al. | 260/837 |
| 4,255,299 | 3/1981 | Daimon et al. | 260/17 |
| 4,267,302 | 5/1981 | Ohmori | 528/103 |
| 4,275,225 | 6/1981 | Krespan | 560/174 |

FOREIGN PATENT DOCUMENTS 54-163985  12/1979  Japan .
6729173  4/1980  U.S.S.R. .

OTHER PUBLICATIONS

T. I. Ito, et al., Div. of Fluorine Chem. Abstracts, Am. Chem. Soc., 1st ACS/CSJ Chemical Congress, Honolulu, Hawaii, Apr. 2-5, 1979, par. 47.
S. P. Khrlakyan, V. V. Shokina, & I. L. Knunyants, Izr. Ak6d. Nauk SSSR, Khim, 1965 (1), 72; C.A. 62, 11753e (1965).
P. Tarrant, C. G. Allison, and K. P. Barthold, "Fluorine Chemistry Reviews", vol. 5, P. Tarrant, Ed., Dekker, New York, NY, 1971, pp. 77-113.

*Primary Examiner*—Norma S. Milestone

[57] ABSTRACT

Perfluoroglycidyl ethers of the formula

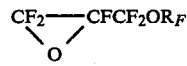

are prepared by epoxidation of a perfluoroallyl ether of the formula

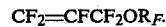

The glycidyl ethers are useful as monomers for preparing polymers which are useful as stable oils and greases. Polymers containing functional moieties which provide crosslinking or cure sites are stable elastomeric materials useful as sealants, caulks, and fabricated objects.

4 Claims, No Drawings

PERFLUOROGLYCIDYL ETHERS

This is a division, of application Ser. No. 250,906, filed Apr. 3, 1981.

TECHNICAL FIELD

This invention relates to perfluoroglycidyl ethers, their preparation and polymers therefrom.

BACKGROUND ART

P. Tarrant, C. G. Allison, K. P. Barthold and E. C. Stump, Jr., "Fluorine Chemistry Reviews," Vol. 5, P. Tarrant, Ed., Dekker, New York, New York (1971) p 77 disclose fluorinated epoxides of the general formula

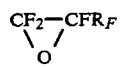

wherein $R_F$ may be a perfluoroalkyl group of up to 10 carbons containing one or more functional substituents $-CF=CF_2$,

—Cl or —H

Oxidations of the type

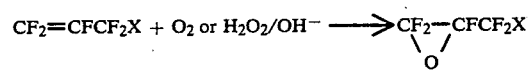

are disclosed where X is —F, —(CF$_2$)$_5$H (U.S. Pat. No. 3,358,003), —CF$_2$Cl or —CF$_2$Br (T. I. Ito et al, Abstracts, Div. Fluoro. Chem., Am. Chem. Soc., 1st ACS/CJS Chem. Congress, Honolulu, HI, April 1979)

Oligomers and polymers of perfluoroepoxides

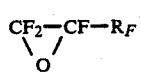

are described in U.S. Pat. No. 3,419,610 and by P. Tarrant et al. in Fluorine Chem. Reviews, 5, pp 96–102 (1971). Nonfunctional fluoroethers of difluoroacetyl fluoride of the formula $R_FOCF_2COF$ are also known, and the insertion of one or more moles of hexafluoropropene epoxide into said nonfunctional perfluoroethers is disclosed in U.S. Pat. No. 3,250,808:

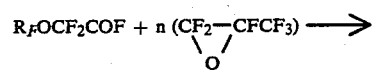            (1)

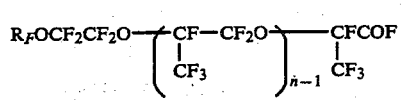

where n is 1 to at least 6 and $R_F$ is perfluoroalkyl, perfluoroalkoxy, or perfluoroalkoxyalkyl.

Glycidyl ethers containing the segment

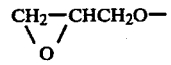

are widely disclosed. The glycidyl ether

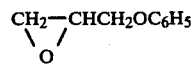

is disclosed in U.S. Pat. No. 4,127,615.

DISCLOSURE OF INVENTION

Novel perfluoroglycidyl ethers are provided having the general formula

    I wherein $R_F$ is:

(i)

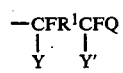

wherein $R^1$ is a carbon-carbon bond or a linear or branched perfluoroalkylene group of 1 to 12 carbon atoms; Q is —SO$_2$F, —COF, —F, —Cl, —Br, —I, —CN, —CO$_2$H, —OC$_6$F$_5$, or —CO$_2$R$^4$ where R$^4$ is —CH$_3$ or —C$_2$H$_5$; Y and Y' are —F or —CF$_3$, provided that only one of Y and Y' can be —CF$_3$; or (ii) —CF(R$^2$)$_2$
wherein $R^2$ is —F, —CF$_2$Cl, —CF$_2$Cn, —CF$_2$COF, —CF$_2$CO$_2$H, —CF$_2$OCF(CF$_3$)$_2$ or —CF$_2$CO$_2$R$^4$ where R$^4$ is defined as above; or (iii)

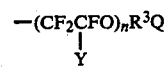

wherein $R^3$ is a linear or branched perfluoroalkylene group of carbon content such that the moiety

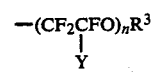

does not exceed 15 carbon atoms; Y independently is —F or —CF$_3$; n is 1 to 4; and Q is as defined above; or (iv) —C$_6$F$_5$.

Perfluoroglycidyl ethers of formula I are prepared by contacting and reacting the corresponding polyfluorallyl ethers with oxygen.

The ethers of formula I may be homopolymerized, or copolymerized with suitable fluorinated epoxides which include hexafluoropropene oxide, tetrafluoroethylene oxide, and other perfluoroglycidyl ethers of formula I.

Homo- and copolymers prepared from formula I ethers wherein $R_F$ is nonfunctional are useful as stable oils and greases. Polymers prepared from formula I ethers wherein $R_F$ contains functional moieties which may provide crosslinking or cure sites are stable elastomeric materials useful as sealants, caulks, and fabricated objects. Preferred ethers of formula I are those which contain functional moieties within $R_F$. Especially preferred are ethers of formula I where $R_F$ is $-C_6F_5$, $$-\underset{Y}{\underset{|}{C}}FR'\underset{Y'}{\underset{|}{C}}FQ$$

or $-CF(R^2)_2$, Y and Y' are $-F$; Q is $-SO_2F$, $-CO_2R^4$, $-CN$, $-OC_6F_5$, $-Br$, $-I$ and $-COF$; $R^2$ is $-CF_2CO_2R^4$, $-CF_2COF$, $-CF_2CN$; and $R^4$ is $-CH_3$ or $-C_2H_5$.

Perfluoroallyl ethers, when reacted with $O_2$, also yield, in addition to the perfluoroglycidyl ethers of formula I, coproduct fluoroformyl difluoromethyl ethers containing one less carbon atom which have the general formula $$FOC-CF_2OR_F \qquad \text{II}$$

wherein $R_F$ is as defined above.

The novel perfluoroglycidyl ethers of this invention are prepared from the perfluoroallyl ethers which are disclosed by Krespan in U.S. application Ser. No. 145,756, filed May 1, 1980 now U.S. Pat. No. 4,275,225. These perfluoroallyl ethers are of the formula $CF_2=CFCF_2OR_F$
wherein $R_F$ is:
(i)

$$-\underset{Y}{\underset{|}{C}}FR^1\underset{Y'}{\underset{|}{C}}FQ$$

wherein $R^1$ is a carbon-carbon bond or a linear or branched perfluoroalkylene group of 1 to 12 carbon atoms; Q is $-SO_2F$, $-COF$, $-F$, $-Cl$, $-Br$, $-I$, $-CN$, $-CO_2H$, $-OC_6F_5$, or $-CO_2R^4$ where $R^4$ is $-CH_3$ or $-C_2H_5$; Y and Y' are $-F$ or $-CF_3$, provided that only one of Y and Y' can be $-CF_3$; or (ii) $-CF(R^2)_2$
wherein $R^2$ is $-F$, $-CF_2Cl$, $-CF_2CN$, $-CF_2COF$, $-CF_2CO_2H$, $-CF_2OCF(CF_3)_2$ or $-CF_2CO_2R^4$ where $R^4$ is defined as above; or (iii)

$$-(CF_2\underset{Y}{\underset{|}{C}}FO)_nR^3Q$$

wherein $R^3$ is a linear or branched perfluoroalkylene group of carbon content such that the moiety $$-(CF_2\underset{Y}{\underset{|}{C}}FO)_nR^3$$

does not exceed 15 carbon atoms; Y is $-F$ or $-CF_3$; n is 1 to 4; and Q is as defined above; or (iv) $-C_6F_5$.

The perfluoroglycidyl ethers of this invention are also prepared from perfluoroallyl ethers of the formula $$CF_2=CFCF_2O(CF_2\underset{Y}{\underset{|}{C}}FO)_nR^3Q$$

wherein $R^3$, Q and n are as defined under (iii) above, and Y, independently, can be $-F$ or $-CF_3$.

These perfluoroallyl ethers are prepared by
(1) mixing and reacting
   (a) a carbonyl compound having the formula:

$$\underset{}{\overset{O}{\overset{\|}{A^1-C-Y}}}$$

wherein $A^1$ is $$\underset{Y'}{\underset{|}{Q'CFR^1-}}$$

where $R^1$ is a carbon-carbon bond or a linear or branched perfluoroalkylene group of 1 to 12 carbon atoms; Q' is $-SO_2F$, $-SO_2OCF_2CH_3$, $-COF$, $-F$, $-Cl$, $-Br$, $-I$, $-CN$, $-OC_6F_5$ or $-CO_2R^4$ where $R^4$ is $-CH_3$ or $-C_2H_5$; Y and Y' are $-F$ or $-CF_3$, provided that only one of Y and Y' can be $-CF_3$; or (b) a carbonyl compound having the formula:

$$\underset{}{\overset{O}{\overset{\|}{A^2-C-F}}}$$

wherein $A^2$ is $$Q'R^3(O\underset{Y}{\underset{|}{C}}FCF_2)_{n-1}O\underset{Y}{\underset{|}{C}}F-$$

where $R^3$ is a linear or branched perfluoroalkylene group of carbon content such that the moiety $$R^3(O\underset{Y}{\underset{|}{C}}FCF_2)_{n-1}O\underset{Y}{\underset{|}{C}}F-$$

does not exceed 14 carbon atoms; Y independently is $-F$ or $-CF_3$; n is 1 to 4; and Q' is defined as above; or (c) an alkali metal salt of pentafluorophenol, with a metal fluoride of the formula MF where M is $K-$, $Rb-$, $Cs-$, or $R_4N-$ where each $-R$, alike or different, is alkyl of 1 to 6 carbon atoms; and (2) mixing the mixture from (1) with a perfluoroallyl compound of the formula $$CF_2=CF-CF_2Z$$

wherein
Z is $-Cl$, $-Br$ or $-OSO_2F$.

The perfluoroglycidyl ethers of formula I and the fluoroformyl difluoromethyl ethers of formula II are prepared from the perfluoroallyl ethers by reaction with oxygen at about 20° to about 200° C., preferably about 80° to about 160° C.:

$$CF_2=CFCF_2OR_F \xrightarrow{O_2} \quad (2)$$

$$(x)\ CF_2\!\!-\!\!\underset{O}{\underset{\diagdown\diagup}{CFCF_2OR_F}} + (y)\ FOC\!\!-\!\!CF_2OR_F + (y)\ COF_2$$
$$\qquad\qquad I \qquad\qquad\qquad II$$

where x and y are, respectively, the mole fractions of products I and II. Ethers of formula I are normally stable at the reaction temperature. Formation of ethers of formula II, together with carbonyl fluoride, is presumed to result from oxidative cleavage of the allylic double bond in the starting polyfluoroallyloxy compound.

The by-product $COF_2$ is normally inert, except where $R_F$ contains a functional group such as $-CO_2H$ with which it can react; e.g.

$$CF\!\!-\!\!\underset{O}{\underset{\diagdown\diagup}{CF_2CF_2O(CF_2)_5CO_2H}} + COF_2 \longrightarrow \quad (3)$$

$$CF_2\!\!-\!\!\underset{O}{\underset{\diagdown\diagup}{CFCF_2O(CF_2)_5COF}} + HF + CO_2$$

The epoxidation reaction may be carried out at pressures of about 5 to about 3000 psi, preferably about 50 to about 1500 psi. Solvents are not essential, but inert diluents such as 1,1,2-trichloro-1,2,2-trifluoroethane ($CFCl_2CF_2Cl$) or perfluorodimethylcyclobutane may be used.

Reactant proportions may vary from a large molar excess of olefin over $O_2$ (e.g., 100:1) to a large excess of $O_2$ over olefin (e.g., 100:1); a modest excess of $O_2$, e.g., about 1.1:1 to about 10:1, is normally preferred to insure complete reaction of the olefin.

The epoxidation reaction is most conveniently initiated thermally, but may be catalyzed by the use of free-radical initiators or by ultraviolet irradiation in the presence of a photoactive material such as bromine. The epoxidation may be conducted in a batchwise or continuous manner.

The epoxidation product of formula I is generally isolated by direct fractional distillation, although in some cases a preliminary treatment with $Br_2$ or $Cl_2$ may be helpful. When epoxidation is carried out at lower temperatures (100°), addition of radical acceptors such as o-dichlorobenzene to the mixture just prior to fractionation is a desirable precaution against the possible presence of peroxides.

The art teaches the preparation of certain fluoroepoxides, such as hexafluoropropylene oxide (HFPO), by reacting the corresponding vinyl compound with alkaline hydrogen peroxide. Said reagent cannot be used for preparing the perfluoroglycidyl ethers of formula I when $R_F$ contains a functional group such as $-CO_2H$, $-CO_2R^4$, $-COCl$, or $-COF$ which is hydrolytically unstable in the presence of alkaline $H_2O_2$. Where $R_F$ is nonfunctional or contains functional groups which are inert or relatively unreactive to alkaline $H_2O_2$, such as $-Br$, said reagent can be used as an alternative to molecular oxygen for preparing formula I compounds.

Perfluoroglycidyl ethers of formula I can be homopolymerized or copolymerized with suitable fluorinated epoxides such as HFPO, tetrafluoroethylene epoxide (TFEO) and other perfluoroglycidyl ethers of formula I; HFPO and TFEO are preferred comonomers, with HFPO most preferred. For example:

$$xCF_3CFCF_2 + R_FOCF_2CF\!\!-\!\!CF_2 \xrightarrow[\text{catalyst, }-30°\text{ C.}]{\text{anionic}} \quad (4)$$
$$\quad\underset{O}{\underset{\diagdown\diagup}{\phantom{xCF_3CFCF_2}}} \qquad \underset{O}{\underset{\diagdown\diagup}{\phantom{R_FOCF_2CFCF_2}}}$$
$$\qquad I$$

$$\left[\left(\!\!\!\begin{array}{c}CF_3\\|\\-CFCF_2O-\end{array}\!\!\!\right)_{\!x}\!\!\left(\!\!\!\begin{array}{c}CF_2OR_F\\|\\-CF-CF_2O-\end{array}\!\!\!\right)\right]_{\!n}$$
$$\qquad\qquad III$$

wherein x is moles of HFPO per mole of formula I ether, which monomer units may be randomly distributed within the copolymer. (Co)-polymerization proceeds in the presence of a suitable solvent and initiator at temperatures of about −45° to about +25° C., preferably about −35° to about 0° C. The quantity of solvent may be from about 5 to about 40 mole percent of the total monomer feed. Suitable solvents include commercial ethers such as diethyl ether, diglyme, triglyme and tetraglyme (di-, tri-, and tetraethyleneglycol dimethyl ether), and fluorinated solvents such as 1,1,2-trichlorotrifluoroethane, chlorotrifluoroethylene, dichlorodifluoromethane, hydrogen-capped HFPO oligomers of the formula $CF_3CF_2CF_2O[CF(CF_3)CF_2O]_nCHFCF_3$, wherein n is 1 to 6, dimers and trimers of hexafluoropropene (HFP), and HFP itself; the latter is a preferred solvent. Solvents should be thoroughly dried, preferably by means of molecular sieves, before use.

Catalysts suitable for the (co)polymerization of formula I ethers include anionic initiators which are effective for the polymerizatin of hexafluoropropylene oxide (HFPO), such as carbon black or, preferably, combinations CsF-LiBr, KF-LiBr, $(C_6H_5)_3PCH_3$, $-LiBr$, CsF-FOCCF($CF_3$)OCF$_2$CF$_2$OCF($CF_3$)COF, CsF-CF$_3$CF$_2$CF$_2$O[CF(CF$_3$)CF$_2$O]$_n$CF($CF_3$)COF, where n is 2 to 6; the latter catalyst wherein n is 4 to 6 is preferred. Preparation of fluoropolyethers such as that used in the last mentioned catalyst is described in U.S. Pat. No. 3,322,326. Catalyst concentration should be about 0.05 to about 1 mole percent of the total monomer feed when higher molecular weight products are desired.

The perfluoroglycidyl ethers of formula I and comonomers such as HFPO should be reasonably pure and dry before (co)polymerization. Monomers may be dried with molecular sieves or, preferably, over KOH-CaH$_2$. Dryness and high purity are necessary for the preparation of high molecular weight (co)polymers from formula I ethers.

Polymerization pressures may be in the range of from less than one atmosphere to about 20 atmospheres or more; pressures in the vicinity of one atmosphere are normally preferred.

Copolymers of the present invention containing the functional groups $-COCl$, $-CONH_2$, $-SO_2OH$, $-SO_2OM'$, $-CO_2M'$, or $-CN$, where M' is alkali metal, ammonium or quaternary ammonium, can be prepared by post-polymerization conversion of functional groups, i.e., by reacting copolymers of the present invention containing the functional groups $-COF$, $-COOH$ or $-SO_2F$ with appropriate reagents. For example, copolymers of the present invention containing $-COCl$ groups can be prepared from the corresponding copolymer containing $-COOH$ groups by refluxing with thionyl chloride (SOCl$_2$) in the presence of a catalytic amount of dimethylformamide. Copolymers containing —CONH$_2$ groups can be prepared from the corresponding copolymer containing —COOH, —COF, —COCl or —CO$_2$R$^4$ groups by esterification and/or ammonolysis. Copolymers containing —SO$_2$OH or —SO$_2$OM' groups can be prepared hydrolytically from the corresponding copolymers containing —SO$_2$F groups as disclosed in U.S. Pat. No. 3,282,875. Copolymers containing —CO$_2$M' groups can be prepared hydrolytically from the corresponding copolymers containing —COF groups as disclosed in U.S. Pat. No. 4,131,740. Copolymers containing —CN groups can be prepared from the corresponding copolymers containing —CONH$_2$ groups by reaction with a reagent of the formula

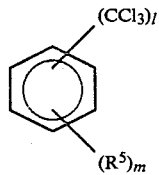

where R$^5$ is —CH$_3$ or —C$_2$H$_5$, l is 1 or 2 and m is 0, 1 or 2, to yield copolymer containing —CN moieties; benzotrichloride is a preferred reagent. Nitrile functions are well suited for providing cure sites in the copolymers of this invention, leading to stable elastomeric materials as described above.

Thus, this invention provides copolymers containing recurring units of the formula

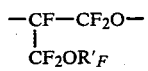

where R'$_F$ has the same meaning as R$_F$, defined above, except that the functional group selection also includes —COCl, —CONH$_2$, —SO$_2$OH, —SO$_2$OM', and —CO$_2$M'. The functional groups —CO$_2$M', —SO$_2$OM', and —SO$_2$OH impart hydrophilicity and cation-exchange properties to the polymers of the present invention. The acid chloride functional group is a precursor to other useful carboxylated groups, e.g., —COOH, —CO$_2$R$^4$, and —CO$_2$M'. The amide functional group is a precursor to the —CN group, which provides useful cure sites in fluoroelastomers.

In the following examples of specific embodiments of the present invention, parts and percentages are by weight and all temperatures are in degrees C. unless otherwise specified. Example 2B represents the best mode contemplated for carrying out the invention.

EXAMPLE 1

Perfluoro-(1,2-epoxy-5-methyl-4-oxahexane)

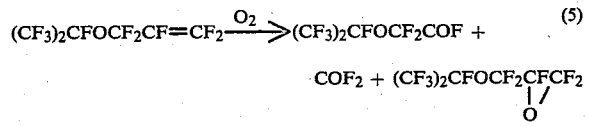

A. A 100-ml stainless steel tube was charged with 63.2 g (0.20 mol; 39 ml) of (CF$_3$)$_2$CFOCF$_2$CF=CF$_2$ and 50 ml of CFCl$_2$CFCl$_2$ and pressured with O$_2$ to 200 psi. When heated slowly, the system showed an obvious loss in pressure near 75°. Temperature was held at ca. 80° and O$_2$ was pressured in as needed to maintain 250 psi over a total of 17 h. Distillation of the liquid products gave 12.0 g (21%) of byproduct acid fluoride, bp 40°–43°, and 17.3 g (26%) of perfluoro-2-methyl-5,6-epoxy-3-oxahexane, by 57°–59°.

Redistillation, of the epoxide gave a nearly pure sample, bp 58.5°–59°. IR(CCl$_4$): 6.47 (epoxide), 7.5–9μ (CF, C-O) with a trace COF impurity at 5.31μ. NMR: $^{19}$F −81.6 (t of d, J$_{FF}$ 5, 2.0 Hz, 6F, CF$_3$), −146.0 (t of septets, J$_{FF}$21.6, 2 Hz, 1F, (CF$_3$)$_2$CF) and −156.0 ppm (d of d of t, J$_{FF}$ 19.2, 16.9, 2.8 Hz, 1F, ring CF) with broad AB multiplet for OCF$_2$ centered at −7335 Hz and satellites at −7175 Hz and −7496 Hz; and AB pattern for ring CF$_2$ at −104416 and −10458 Hz (d of t, J$_{FF}$19.2, 9.7 Hz, 1F) and −10628 and −10669 Hz (d, J$_{FF}$16.9 Hz, 1F). Trace impurities were present, as was also indicated by gc analysis.

Anal. Calcd for C$_6$F$_{12}$O$_2$: C, 21.70; F, 68.66 Found: C, 21.00; F, 68.23.

B. Oxidation at a higher temperature than that employed in Part A was carried out in an attempt to maximize epoxide formation. A 100-ml tube charged with 56.9 g (0.18 mol, 35 ml) of (CF$_3$)$_2$CFOCF$_2$CF=CF$_2$ and 50 ml of CFCl$_2$CFCl$_2$ was preheated to 140° and 110 psi before addition of O$_2$. As O$_2$ was added in slugs, rapid exothermic reaction occurred. Temperature control was maintained better with slow continuous feed of O$_2$ between 220–260 psi; after 8 h the pressure remained constant at 260 psi. Fractionation of the liquid products gave 7.9 g (16%) of crude acid fluoride, bp 38°–45°, and 34.6 g (58%) of epoxide, bp 58°–61°. Gc and ir indicated 6–7% impurities to be present, including ca. 5% of CFCl$_2$CFCl$_2$ solvent.

EXAMPLE 2

Perfluoro-5,6-epoxy-3-oxahexanesulfonyl Fluoride

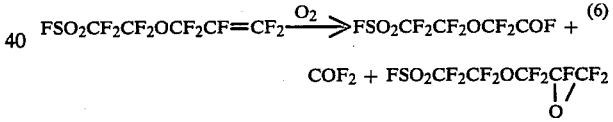

A. A 100-ml stainless steel tube charged with 68.1 g (0.206 mol, 40 ml) of FSO$_2$CF$_2$CF$_2$OCF$_2$CF=CF$_2$, 50 ml of CF$_2$ClCFCl$_2$, and 200 psi of O$_2$ was heated to 80° and 300 psi. The tube was repressured periodically with O$_2$ until pressure was constant at 300 psi (13 h). Forty ml of o-dichlorobenzene was added to the liquid product, and the mixture was fractionated to give 11.4 g (19%) of acid fluoride, bp 48°–52° (200 mm), and crude epoxide, bp 58°–70° (200 mm).

Redistillation of the crude perfluoro-5,6-epoxy-3-oxahexanesulfonyl fluoride gave 13.1 g (18%), bp 59°–61° (200 mm). IR (neat): 6.51 (epoxide), 6.82 (SO$_2$F), 7.5–9μ (CF, C-O). NMR: $^{19}$F 45.2 (t of t, J$_{FF}$ 6.1, 6.1 Hz, 1F, SO$_2$F), −82.5 (m, 2F, CF$_2$CF$_2$O), −113.1 (d of t, J$_{FF}$ 5.6, 2.8 Hz, 2F, SO$_2$CF$_2$), and −156.8 ppm (d of d of m, J$_{FF}$18.8 Hz, 1F, ring CF) with AB multiplet for OCF$_2$ at −7351, −7503, −7539 and −7689 Hz (m, 2F) and an AB multiplet for ring CF$_2$ at −10365 and −10405 Hz (d of t, J$_{FF}$ 18.8, 9.8 Hz, 1F) and −10593 and −10633 Hz (d, J$_{FF}$ 16.8 Hz, 1F).

Anal. Calcd for C$_5$F$_{10}$O$_4$S: C, 17.35; S, 9.27, Found: C, 17.19; S, 9.95.

B. A purer sample of epoxide than that in Part A was obtained in higher yield by oxidation of neat olefinic precursor. A 100-ml metal tube containing 134.9 g (0.41 mol, 80 ml) of $FSO_2CF_2CF_2OCF_2CF=CF_2$ was held at 140°–150° while oxygen was added slowly and continuously for 2 h. Pressure rose from 75 psi to 250 psi and leveled. The pressure was raised to 450 psi with $O_2$, no further pressure change occurred in 5 h. The additional oxygen and higher pressure were used to insure complete reaction. Ten ml of o-dichlorobenzene was added to the liquid product, and the mixture was fractionated to give 32.0 (26%) of crude acid fluoride, bp mainly 80°, and 80.5 g (57%) of epoxide, bp 57.65° (200 mm). Redistillation gave 69.5 g (49%), bp 93°–94°, of pure epoxide.

Anal. Calcd for $C_5F_{10}O_4S$: C, 17.35; S, 9.27 Found: C, 17.60; S, 9.52.

EXAMPLE 3

Perfluoro-9,10-epoxy-7-oxadecanoic Acid and Perfluoro-9,10-epoxy-7-oxadecanoyl Fluoride

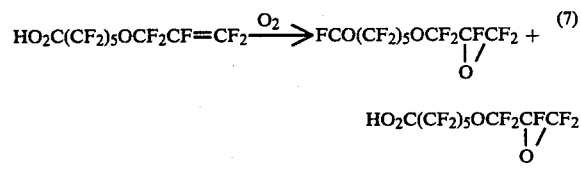

A. A 100-ml tube charged with 117 g (0.26 mol, 65 ml) of $HO_2C(CF_2)_5OCF_2CF=CF_2$ was heated at ca. 140° while oxygen was added slowly until no exothermic reaction was apparent. Further heating at 140° gave a pressure rise from 332 to 418 psi over 1–2 h. Ten ml of o-dichlorobenzene was added to the liquid product, and the mixture was distilled. Fractions collected at 68°–98° (100 mm) had a small second layer of o-dichlorobenzene which was removed, and the crude perfluoro-9,10-epoxy-7-oxadecanoyl fluoride was refractionated to give 23.2 g (19%) of epoxy acid fluoride, bp 73°–75° (100 mm). IR (neat): 5.30 (COF), 6.47 (epoxide), 7.8–9μ (CF, C-O). NMR $^{19}F$ 23.9 (t of t, $J_{FF}$ 8, 6, 1.5 Hz, 1F, COF), $-83.6$ (m, 2F, $CF_2CF_2O$), $-119.0$ (t of d of m, $J_{FF}$ 12, 8 Hz, 2F, $CF_2COF$), $-122.6$ (m, 2F, $CF_2$), $-123.4$ (m, 2F, $CF_2$), $-126.2$ (m, 2F, $CF_2$), and $-157.0$ ppm (t of m, $J_{FF}$ 18 Hz, 1F, ring CF), with AB multiplets for $OCF_2$ at $-7389$, $-7541$, $-7571$, and $-7723$ Hz (m, 2F) and for ring $CF_2$ at $-10396$ and $-10437$ Hz (d of t, $J_{FF}$ 19.0, 9.9 Hz, 1F) and $-10616$ and $-10657$ Hz (d, $J_{FF}$ 16.9 Hz, 1F).

Anal. Calcd for $C_9F_{16}O_3$: C, 23.49 Found: C, 23.77.

B. Further fractionation of the reaction mixture gave, after removal of o-dichlorobenzene at 45°–55° (5 mm), 34.4 g (29%) of perfluoro-9,10-epoxy-7-oxadecanoic acid, bp 63°–65° (0.6 mm). IR (neat): 2.8–4.0 (H-bonded OH), 5.63 (C=O), 6.48 (epoxide), and 7.3–9μ (CF, C-O). NMR: $^1H$ 12.0 ppm (s, $CO_2H$); $^{19}F$ $-83.6$ (m, 2F, $CF_2CF_2O$), $-119.8$ (t of t, $J_{FF}$ 13, 3.0 Hz, 2F, $CF_2CO_2H$), $-122.6$ (m, 2F, $CF_2$), $-123.3$ (m, 2F, $CF_2$), $-126.2$ (m, 2F, $CF_2$), and $-156.9$ ppm (t of m, $J_{FF}\sim 18$ Hz, 1F, ring CF) with AB multiplets for $OCF_2$ at $-7389$, $-7572$, and $-7723$ Hz (m, 2F) and for ring $CF_2$ at $-10392$ and $-10434$ Hz (d of t, $J_{FF}$ 19.0, 10.0 Hz, 1F) and $-10613$ and 10655 Hz (d, $J_{FF}$ 16.9 Hz, 1F).

Anal. Calcd for $C_9HF_{15}O_4$: C, 23.60; H, 0.22 Found: C, 23.99; H, 0.39.

EXAMPLE 4

Perfluoro-6,7-epoxy-4-oxaheptanenitrile

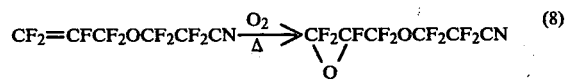

A 100-ml stainless steel-lined tube charged with 38.5 g (0.14 mol) of perfluoro-4-oxa-6-heptenenitrile was heated at 140° while oxygen was added incrementally (over 5.5 h) until reaction was complete. Fractionation of the liquid products gave perfluoro-6,7-epoxy-4-oxaheptanenitrile, bp 65°–67°, 15.7 g (39%). IR ($CCl_4$); 4.40 (CN), 6.47 (epoxide) and 8–9μ (CF, C-O). NMR ($CCl_4$): $-87.5$ (m, 2F, $OCF_2$), $-109.2$ (t, $J_{FF}$ 4.7 Hz, 2F, $CF_2CN$), and $-156.7$ ppm (d of d of m, $J_{FF}$ 18.7, 16.7 Hz, 1F, CF) with AB groupings for ring $CF_2$ at $-10347$ and $-10389$ Hz (d of t, $J_{FF}$ 18.7, 9.5 Hz, 1F) and $-10570$ and $-10610$ Hz (d, $J_{FF}$ 16.7 Hz, 1F) and for $CF_2$ adjacent to epoxide ring at $-7376$, $-7529$, $-7556$, and $-7707$ Hz (m, 2F).

Anal. Calcd for $C_6F_9NO_2$: C, 24.93; N, 4.85 Found: C, 25.19; N, 5.02.

EXAMPLE 5

Perfluoro(phenyl glycidyl)ether

A.
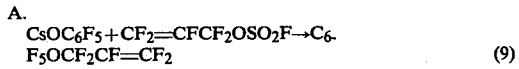

Pentafluorophenyl perfluoroallyl ether was obtained by adding perfluoroallyl fluorosulfate rapidly to an equivalent of cesium pentafluorophenoxide in diglyme at $-25°$. The temperature carried to $+10°$, and the product was isolated by drowning the reaction mixture in water, washing the lower layer with water, and drying and distilling, bp 63° (30 mm). Gc showed the olefin to be 96% pure.

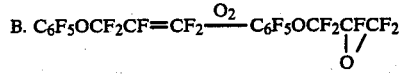

A 100-ml metal tube charged with 64.0 g (0.204 mol) of pentafluorophenyl perfluoroallyl ether was heated at 140° while oxygen was pressured in until uptake ceased. Distillation gave $-4.0$ g of a mixture of pentafluorophenyl pentafluoro-2,3-epoxypropyl ether and starting material, bp 60°–65° (30 mm). This distillate was stirred with 40 ml of $CFCl_2CF_2Cl$ and 16 g (0.10 mol) of bromine while the mixture was irradiated with a sunlamp at 40°–55° for 18 min. Distillation gave nearly pure epoxide, bp 61°–64° (30 mm), 25.5 g. the several fractions were contacted with calcium hydride while open to the air until the acid fluoride impurity peak in the infrared spectrum disappeared, then subjected to vacuum transfer, contact with $CaSO_4$, and filtration to give 14.8 g (22%) of purified epoxide. IR (neat): 3.29, 3.70, 4.01 (weak bands associated with arom. ring), 6.07, 6.30, 6.57 (arom. C=C), 6.47 (epoxide ring) and 8–9μ (CF, C-O). NMR ($CCl_4$): $^1H$ none; $^{19}F$ $-151.8$ (m, 2F, arom. CF), $-155.1$ (t, $J_{FF}$ 21.1 Hz, 1F, arom. CF), $-155.7$ (t, $J_{FF}$ 18 Hz, 1F, epoxide ring CF), and $-161.6$ ppm (m, 2F, arom. CF), with AB patterns for $CF_2$ adjacent to epoxide ring at $-7457$, $-7598$, $-7629$, and $-7771$ Hz (m, 2F) and for ring CF$_2$ at −10365 and −10406 (d of t, J$_{FF}$ 18.6, 9.1 Hz, 1F) and −10610 and 10650 Hz (d, J$_{FF}$ 17.5 Hz, 1F).

Anal. Calcd. for C$_9$F$_{10}$O$_2$: C, 32.75; F, 57.56 Found: C,, 32.89; F, 57.65

EXAMPLE 6

Perfluoro-8,9-epoxy-6-oxanonanoyl Fluoride

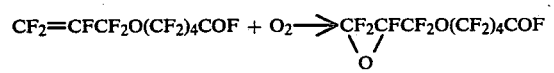 (10)

90.5 g (0.23 mol) of CF$_2$=CFCF$_2$O(CF$_2$)$_4$COF was reacted with small amounts of O$_2$ until 200 psi pressure was obtained at 140°. Pressure was increased with O$_2$ up to 500 psi and maintained for 4 h at 140°. Distillation of the crude mixture gave 35.3 g (37%) of perfluoro-8,9-epoxy-6-oxanonanoyl fluoride, bp 66°–67° (150 mm). IR (CCl$_4$):

5.3 (COF). 6.5 (CF$_2$CF—), 8.9μ (CF, CO). A weak band at 5.55μ indicated the presence of a small amount of unreacted olefin. NMR: $^{19}$F (CFCl$_3$):

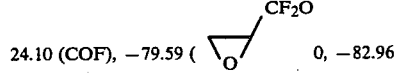

24.10 (COF), −79.59 (  0, −82.96

(OCF$_2$(CF$_2$)$_3$COF), −110.31 and 112.90 (CF$_2$CF), −118.31,

−122.74, −125.05 (CF$_2$CF$_2$CF$_2$COF),

−156.38 ppm (CF$_2$CF).

The $^{19}$F NMR also showed small amounts of unreacted starting material.

EXAMPLE 7

Perfluoro(methyl-8,9-epoxy-6-oxanonanoate)

CF$_2$=CFCF$_2$O(CF$_2$)$_4$COOCH$_3$ + O$_2$ ⟶ (11)

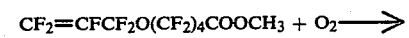

33 g (0.085 mol) of perfluoro(methyl-6-oxa-8-nonenoate) was reacted with oxygen at 140° in the usual manner. Distillation of the crude product gave 3.46 g (10%) of perfluoro(methyl-8,9-epoxy-6-oxanonanoate), bp = 51–52° (1.2 mm). IR (CCl$_4$): 3.28, 3.35, 3.45 (—CH$_3$), 5.57

(C=O), 6.5 (CF$_2$CF—), 7.5 to 9.5μ (CF, CO).

NMR (CFCl$_3$): $^{19}$F −77.56 ( 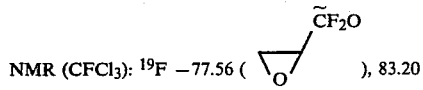 ), 83.20

(OCF$_2$(CF$_2$)$_3$COOCH$_3$), −110.31 −112.77 (CF$_2$CF), −119.08,

−128.18, −125.48 (CF$_2$CF$_2$CF$_2$COOCH$_3$), −156.27 ppm (CF$_2$CF); $^1$H 1.9 ppm (CH$_3$). 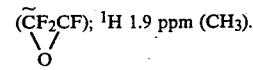

EXAMPLE 8

Perfluoro(9,10-epoxy-5-methyl-4,7-dioxadecanenitrile)

A. CH$_3$OCCF$_2$CF$_2$OCFCF$_2$OCF$_2$CF=CF$_2$ $\xrightarrow{Br}$ $\xrightarrow{NH_3}$ (12)

$\xrightarrow[\text{(CF}_3\text{CO)}_2\text{O}]{\text{pyr.}}$ NCCF$_2$CF$_2$OCFCF$_2$OCF$_2$CFBrCF$_2$Br 

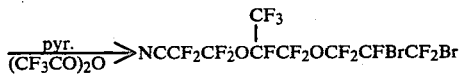

A mixture of 52.4 g (0.111 mol) of methyl perfluoro(5-methyl-4,7-dioxa-9-decenoate), 17.7 g (0.111 mol) of bromine, and 50 ml of CCl$_4$ was stirred and irradiated with a sunlamp intermittently until the exotherm subsided. Another 3.1 g (0.02 mol) of bromine was added and the mixture was irradiated for 30 min. Volatiles were removed at 1 mm pressure, 150 ml of ether was added to the residue, and anhydrous ammonia was bubbled into the stirred mixture until an excess was present. Volatiles were removed to 0.5 mm of pressure, the residue was dissolved in a little tetrahydrofuran and filtered. A mixture of the filtrate and 250 ml of tetrahydrofuran was stirred at −20° while there was added successively 19.3 g (0.244 mol) of pyridine and 24.2 g (0.122 mol) of trifluoroacetic anhydride. The resulting mixture was stirred at −20° for 30 min and then allowed to come to 25°. Dilution with 1 liter of water gave an organic layer which was washed with 500 ml of water, dried over CaSO$_4$ and distilled. There was thus obtained 36.5 g (55%) of perfluoro(9,10-dibromo-5-methyl-4,7-dioxadecanenitrile), bp 62° (10 mm). IR (neat): 4.38 (CN), 8–9μ (CF, C-O). NMR (CCl$_4$): $^{19}$F −80.3 (m, 3F, CF$_3$), −83.9 (m, 2F, CF$_2$O), −85.0 (m, 2F, CF$_2$O), −108.9 (t, J$_{FF}$ 5.4 Hz, 2F, CF$_2$CN), −132.6 (t of t, J$_{FF}$ 14.5, 10.5 Hz, 1F, CFBr), and −145.5 ppm (t of m, J$_{FF}$ 20.9 Hz, 1F, CF) with AB patterns for CF$_2$Br at −5200 and −5375 (d of t, J$_{FF}$ 14.5, 9 Hz, 1F) and −5474 and −5649 Hz (d of t, J$_{FF}$ 14.5, 14.5 Hz, 1F), and for OCF$_2$ at −7001, −7150, −7176, and −7325 Hz (m, 2F).

Anal. Calcd. for C$_9$Br$_2$F$_{15}$NO$_2$: C, 18.05; N, 2.34 Found: C, 18.34; N, 2.29.

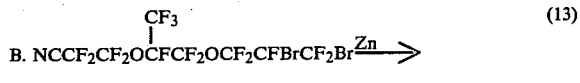 (13)

NCCF$_2$CF$_2$OCFCF$_2$OCF$_2$CF=CF$_2$ (with CF$_3$ on middle CF)

A suspension of 7.58 g (0.116 mol) of zinc dust in 150 ml of diglyme was stirred at 45°–52° (5 mm) while 34.7 g (0.058 mol) of the dibromide was added dropwise. Stirring and heating were continued for one h. The crude product which collected in a −80° trap was washed with 200 ml of water, dried over CaSO$_4$ and distilled to give 16.7 g (66%) of perfluoro(5-methyl-4,7-dioxa-9-decenenitrile), bp 64° (100 mm). IR (neat): 4.39 (CN), 5.58 (C=C), and 8–9μ (CF, C-O). NMR (CCCl$_4$): $^{19}$F −72.2 (d of d of t of d, J$_{FF}$ 24.9, 13.9, ~13.9, 7.9 Hz, 2F, OCF$_2$C=), −80.8 (m, 3F, CF$_3$), −84.2 (m, 2F, OCF$_2$), −85.4 (m, 2F, OCF$_2$), −91.5 (d of d of t, J$_{FF}$ 51.6, 39.5, 7.9 Hz, 1F, cis-CF$_2$CF=CFF), −105.2 (d of d of t, J$_{FF}$ 118.2, 51.6, 24.9 Hz, 1F, trans-CF$_2$CF=CFF), −109.3 (t, J$_{FF}$ 5.3 Hz, 2F, CF$_2$CN), −145.8 (t of m), J$_{FF}$ 16.3 Hz, 1F, CF), and −191.2 ppm (d of d of t, J$_{FF}$ 118.2, 39.5, 13.9 Hz, 1F, —CF$_2$CF=).

Anal. Calcd. for C$_9$F$_{15}$NO$_2$: C, 24.62; N, 3.19 Found: C, 24.56; N, 2.99

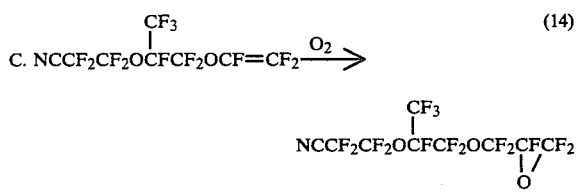

A 100-ml metal tube charged with 89.1 g (0.203 mol) of the cyanoolefin was heated at 140° while oxygen was pressured in until reaction was complete as judged by lack of pressure drop. Fractionation of the liquid product afforded a mixture of cyanoepoxide and cyanoacid fluoride, bp 62° (200 mm) −67° (100 mm). Treatment with CaH$_2$ did not remove the acid fluoride component, so the crude product was shaken with a mixture of 50 ml CFCl$_2$CF$_2$Cl and 300 ml ice and some water. The organic layer was dried over CaSO$_4$, filtered and distilled to give 33.0 g (36%) of pure perfluoro(9,10-epoxy-5-methyl-4,7-dioxadecanenitrile), bp 64°–64.5° (100 mm). IR (neat): 4.37 (CN), 6.47 (peoxide), 8–9μ (CF, C-O). NMR (CCl$_4$): $^{19}$F −80.3 (m, 2F, CF$_2$O), −80.7 (m, 3F, CF$_3$), −83.5 (m, 2F, CF$_2$O), −85.3 (m, 2F, CF$_2$O), −109.2 (t, J$_{FF}$ 5.0 Hz, 2F, CF$_2$CN), −145.4 (t, J$_{FF}$ 21.1 Hz, 1F, CF), and −157.0 ppm (t, J$_{FF}$ 18.0 Hz, 1F, CF) with an AB pattern for ring CF$_2$ at −10400 and −10441 Hz (d of t, J$_{FF}$ 18.5, 9.6 Hz, 1F) and −10626 and −10667 Hz (d, J$_{FF}$ 16.8 Hz, 1F).

Anal. Calcd. for C$_9$F$_{15}$NO$_3$: C, 23.75; N, 3.08 Found: C, 23.99; N, 3.27.

EXAMPLE 9

Perfluoro(1,2-epoxy-7-phenoxy-4-oxaheptane)

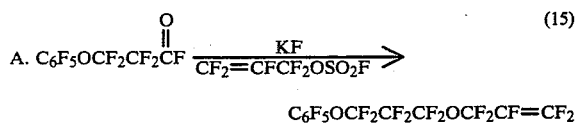

C$_6$F$_5$OCF$_2$CF$_2$CF$_2$OCF$_2$CF=CF$_2$

A suspension of 14.5 g (0.25 mol) of flame-dried KF in 200 ml of diglyme was stirred at 0°–5° while 66.0 g (0.20 mol) of 3-pentafluorophenoxytetrafluoropropionyl fluoride was added. The mixture was stirred an additional 15 min, after which time 50.6 g (0.23 mol) of perfluoroallyl fluorosulfate was added at 0°–5°. The resulting mixture was stirred at 0°–5° for 2 h and then poured into 1 liter of water. The lower layer was washed with 250 ml of water, dried over CaSO$_4$, and fractionated to give 53.2 g (55%) of perfluoro(7-phenoxy-4-oxa-1-heptene), bp 56°–57° (2 mm). IR (neat): 3.32, 3.71, 4.01 (weak, associated with aromatic ring), 5.60 (C=C), 6.07 and 6.59 (arom. C=C), 8–9μ (CF, C-O). NMR (CCl$_4$): $^{19}$F −72.0 (d of d of t of d, J$_{FF}$ 25.1, 13.5, 12, 7.2 Hz, 2F, OCF$_2$C+), −84.6 (m, 4F, CF$_2$O), −91.9 (d of d of t, J$_{FF}$ 52.3, 39.2, 7.2 Hz, 1F, cis-CF$_2$CF=CFF), −105.2 (d of d of t, J$_{FF}$ 117.4, 52.3, 25.1 Hz, 1F, trans-CF$_2$CF=CFF), −129.0 (m, 2F, CF$_2$), −151.7 (m, 2F, arom. CF), −155.2 (t, J$_{FF}$ 21.0 Hz, 1F, arom. CF), −161.7 (m, 2F, arom. CF), and −190.5 ppm (d of d of t of m, J$_{FF}$ 117.4, 39.2, 13.5 Hz, 1F, CF$_2$CF=CF$_2$).

Anal. Calcd. for C$_{12}$F$_{16}$O$_2$: C, 30.03; F, 63.32 Found: C, 30.12; F, 63.25

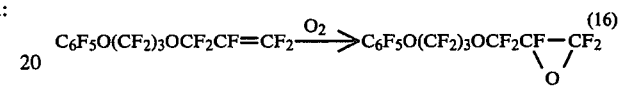

A 100-ml metal tube lined with stainless steel and charged with 105.3 g (0.22 mol) of perfluoro(7-phenoxy-4-oxa-1-heptene) was heated at 140° while oxygen was pressured in intermittently until no pressure drop was observed. The liquid product mixture was fractionated to afford 78.5 g of distillate, bp 37°–70° (3 min). The distillate was shaken with 1 liter of ice water, and then 25 ml of CFCl$_2$CF$_2$Cl and some calcium sulfate were added to hasten separation. The lower layer was dried over calcium sulfate and fractionated to give 33.3 g (31%) of perfluoro(7-phenoxy-1,2-epoxy-4-oxaheptane), bp 55° (1.9 mm). IR (CCl$_4$): 6.47 (epoxide ring), 6.58 (aromatic C=C), 8–9μ (CF, C-O). NMR (CCl$_4$): $^{19}$F −84.1 (m, 2F, OCF$_2$), −84.6 (m, 2F, OCF$_2$), −129.0 (s, 2F, CF$_2$), −151.8 (m, 2F, arom. CF), −155.1 (t, J$_{FF}$ 21.0 Hz, 1F, arom. CF), −156.6 (t, J$_{FF}$ 17.9 Hz, 1F, ring CF), and −161.7 ppm (m, 2F, arom. CF), with AB groupings at −7382, −7534, −7566, and −7719 Hz (m, 2F) for CF$_2$ adjacent to epoxide ring and at −10381 and −10424 Hz (d of t, J$_{FF}$ 18.8, 9.8 Hz, 1F) and −10600 and −10642 Hz (d, J$_{FF}$ 17.3 Hz, 1F) for expoxide CF$_2$.

Anal. Calcd for C$_{12}$F$_{16}$O: C, 29.05, Found: C, 29.40.

EXAMPLE 10

Perfluoro(1-bromo-6,7-epoxy-4-oxaheptane)

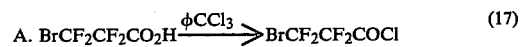

3-Bromotetrafluoropropionic acid was obtained by hydrolysis of the ethyl ester; the latter was prepared as described by Y. K. Kim, J. Org. Chem., 32, 3673 (1967).

A mixture of 375.9 g (1.67 mol) of 3-bromotetrafluoropropionic acid, 10 g of ferric chloride, and 488.7 g (2.50 mol) of benzotrichloride was refluxed for 1.5 h, then crude product was removed, bp about 60°. Redistillation gave 287.9 g (71%) of 3-bromotetrafluoropropionyl chloride, bp 67°–68°. IR (CCl$_4$): 5.53 (C=O).

A suspension of 52.3 g (0.90 mol) of flame-dried KF in 450 ml of diglyme was treated with 140 g (0.844 mol) of hexafluoroacetone to give a solution of potassium heptafluoroisopropoxide. Dropwise addition of 200 g (0.823 mol) of BrCF₂CF₂COCl from part A at ca. 20° was accomplished by gas evolution through a −20° condenser. The mixture was stirred for 1 h, then warmed to 58° to drive off additional HFA through the condenser. Volatile product was transferred to a −80°L trap by heating the pot contents to 90°(50mm). Distillation of the crude product fluoride gave 140 g (75%) of 3-bromotetrafluoropropionylfluoride, bp mainly 28°. IR (gas phase): 5.23μ (COF).

C. BrCF₂CF₂COF + KF + CF₂=CFCF₂OSO₂F ⟶ (19)

BrCF₂CF₂CF₂OCF₂CF=CF₂

A suspension of 35.9 g (0.617 mol) of flame-dried KF in 750 ml of diglyme was stirred at 0° while 140.0 g (0.617 mol) of 3-bromotetrafluoropropionyl fluoride from part B was added. The mixture was stirred at 0°–5° for another 30 min and then was treated with 141.9 g (0.617 mol) of perfluoroallyl fluorosulfate. The reaction mixture was stirred for 4 h at 0°–5° and then poured into 3 liters of water. The resulting lower layer was washed with 500 ml of water, dried over CaSO₄, and distilled to give 132.5 g (57%) of perfluoro(7-bromo4-oxa-1-heptene), bp 96°–99°, trace impurity only by GC. A sample from a similar synthesis was analyzed. IR (CCl₄): 5.59μ (CF=CF₂). NMR (CCl₄): ¹⁹F −64.4 (t of m, $J_{FF}$ 9.9 Hz, 2F, CFBr), −71.9 (d of d of t of d, $J_{FF}$ 24.9, 13.8, ~13, 7.3 Hz, 2F, OCF₂C=), −82.8 (t of t of m, $J_{FF}$~13, 9.9 Hz, 2F, CF₂O), −92.0 (d of d of t of t, $J_{FF}$ 52.0, 39.3, 7.3 Hz, 1F, cis-CF₂CF=CFF), −105.3 (d of d of t, $J_{FF}$ 117.7, 52.0, 24.9 Hz, 1F, trans-CF₂CF=CFF), −121.9 (m, 2F, CF₂), and −190.6 ppm (d of d of t of t, $J_{FF}$ 117.7, 39.3, 13.8, 1.6 Hz, 1F, CF₂CF=).

Anal. Calcd. for C₆BrF₁₁O: C, 19.12; Br, 21.20. Found: C, 19.38; Br, 21.49.

D. BrCF₂CF₂CF₂OCF₂CF=CF₂ + O₂ ⟶ (20)

BrCF₂CF₂CF₂OCF₂CFCF₂
                     \ /
                      O

A 100-ml metal tube containing 20.0 g (0.053 mol) of perfluoro(7-bromo-4-oxa-1-heptene) from Part C and 60 ml of CF₂ClCFCl₂ was heated at 140° while O₂ was injected incrementally over a 4 h period until absorption ceased. The mixture was cooled, gases vented, and the liquid product fractionated to give 6.9 g (33%) of perfluoro(1-bromo-6,7-epoxy-4-oxaheptane), bp 94°–95°. IR (CCl₄): 6.50 (epoxide), 8–9μ (CF, C-O) with weak band indicating COF impurity near 5.3μ. NMR (CCl₄): ¹⁹F −65.6 (t of m, $J_{FF}$ 9.8 Hz, 2F, CF₂Br), −80.2 (AB multiplets 2F, CF₂O), −80.4 (AB multiplets, 2F, CF₂O), −121.9 (m, 2F, CF₂), and −156.6 ppm (t of m, $J_{FF}$ 17.6 Hz, 1F, CF), with AB multiplets for ring CF at −10368 and −10409 Hz (d of d of m, $J_{FF}$ 18.5, 9.8 Hz, 1F) and −10596 and −10637 Hz (d, $J_{FF}$ 17.3 Hz, 1F).

Anal. Calcd. for C₆BrF₁₁O₂: C, 18.34, Found: C, 18.51.

EXAMPLE 11

Copolymerization of Perfluoro-5,6-epoxy-3-oxahexanesulfonyl Fluoride with Hexafluoropropylene Oxide (HFPO)

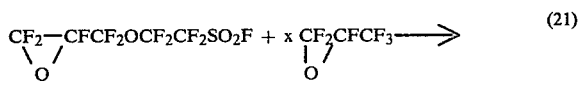

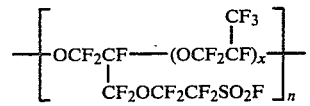
(21)

The polymerization catalyst was prepared by reacting 2.09 g (0.0137 mol) CsF, 6.07 g (0.0273 mol) tetraglyme and 7.97 g (0.0120 mol) HFPO tetramer. The catalyst was shaken for at least 6 h and centrifuged for 30 min at 0°. To a thoroughly dried 4-neck 500-ml flask was injected 4 millimole of the prepared catalyst. The reaction mixture was then cooled to −35° C. Hexafluoropropylene (dried by passing through molecular sieves) was added at a rate of 1 g/min for a total of 20 g. Hexafluoropropylene oxide (dried by passing over KOH and CaH₂) was added at a rate of 0.07 g/min and the epoxysulfonyl fluoride at the rate of 0.13 g/h. After 52.5 h of reaction at −32° to −35° C., the unreacted gases were removed by applying vacuum. The polymer mixture was then brought slowly to 100° under vacuum to remove any unreacted monomers. Weight of the recovered copolymer was 220 g. Part of the highly viscous polymer, 20 g, was reacted with excess ethanol to obtain the corresponding ester end-capped polymer. The molecular weight by IR based on the ester absorption was 42,200. Amount of incorporated epoxysulfonyl fluoride was 4.2% based on S analysis by X-ray fluorescence. x in the formula is approximately 48.

EXAMPLE 12

Cross-linking of the Copolymer 20 g of the copolymer of Example 11, 2 g hexamethylenediamine carbamate, and 2 g MgO were mixed in a 2-roll mill at 50° until a homogeneous blend was obtained. The blend was pressed at 180° in a Carver press and cured for 2 h. The resulting crosslinked solid was rubbery and was virtually unaffected by the "Freon" E₃ solvent. On standing, the solid flowed slightly.

EXAMPLE 13

Copolymerization of Perfluoro-5,6-epoxy-3-oxahexanesulfonyl Fluoride with Hexafluoropropylene Oxide Using the procedure described in Example 11, 132 g of HFPO and 67.15 g of the epoxysulfonyl fluoride were copolymerized at −31.5° to −33°. The viscous polymer gave a molecular weight by IR of 9600. Amount of incorporated comonomer was 18.5% based on S analysis by X-ray fluorescence, and x is about 9.

EXAMPLE 14

Homopolymerization of Perfluoro-5,6-epoxy-3-oxahexanesulfonyl Fluoride

Following the general procedure for HFPO copolymerization, 8.5 g (0.024 mol) of epoxysulfonyl fluoride was polymerized using 0.00072 mol CsF catalyst in the presence of 1.2 g hexafluoropropene. After 4 h reaction at −35°, the polymer was worked up by raising the temperature to 100° at 1 mm to remove unreacted monomer. Weight of the dry polymer was 7.74 g. After conversion to the ester end groups, molecular weight was 2800 (degree of polymerization of 8) by ebullioscopy in $CFCl_2CF_2Cl$.

EXAMPLE 15

Copolymerization of Perfluoro-8,9-epoxy-6-oxanonanoyl Fluoride with Hexafluoropropylene Oxide

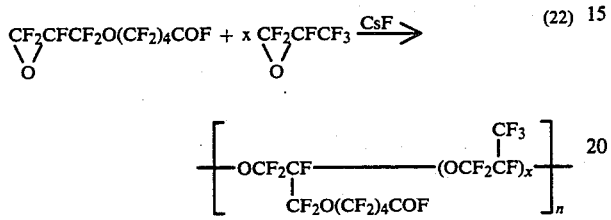

Following the general procedure for HFPO copolymerization, 183.2 HFPO and 4.59 g of the epoxyacid fluoride were polymerized with 3.6 millimoles catalyst over a period of 43.6 h at −32° to −34°. Weight of the recovered polymer was 182 g. By IR in $CFCl_2CF_2Cl$ and allowing for chain transfer, the approximate molecular weight was 40,000. x is approximately 100.

EXAMPLE 16

Copolymerization of Perfluoro-6,7-epoxy-4-oxaheptane-nitrile with Hexafluoropropylene Oxide

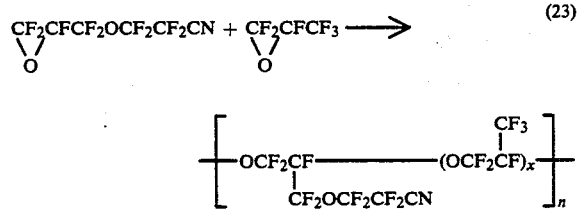

Following the general procedure for HFPO copolymerization (Example 12), 4.68 g of the epoxynitrile of Example 4 and 179 g of HFPO were copolymerized at −33° to −35° over a period of 47.6 hr. The molecular weight by IR was 43,100. The amount of incorporated epoxynitrile was 2.5% by nitrogen analysis. X in the formula is approximately 68.

EXAMPLE 17

Crosslinking of the Copolymer of Hexafluoropropylene Oxide and Perfluoro-6,7-epoxy-4-oxaheptanenitrile The following was milled: 30 g of the copolymer of Example 16, 3 g carbon black and 0.9 g tetraphenyltin. The mixture was degassed at 50°/0.1 mm and heated to 200° under $N_2$ for 60 hr; 260° for 1 day and 300° for 2 days. The result was an elastic solid with some flow on standing.

A better curing was obtained when 0.39 g MgO was added to the above formulation. A rubbery solid was obtained with improved toughness.

EXAMPLE 18

Copolymerization of Perfluoro(phenylglycidyl) Ether with Hexafluoropropylene Oxide

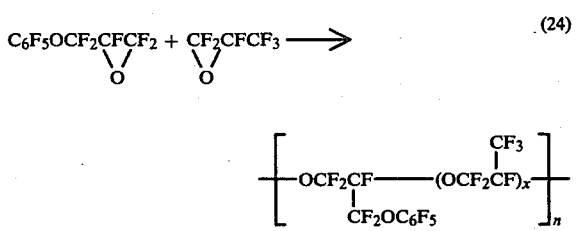

Following the procedure for HFPO copolymerization (Example 12), 7.36 g of the perfluoro(phenylglycidyl) ether prepared as in Example 5 and 138 g of HFPO were copolymerized at −32° to −35° over a period of 48 hr. The molecular weight by IR was 25,000. X in the formula is approximately 49 based on the 5% phenoxy monomer added during the polymerization.

EXAMPLE 19

Crosslinking of the Copolymer of Perfluoro(phenylglycidyl) Ether and Hexafluoropropylene Oxide The following was milled until a homogeneous mixture was obtained: 5.2 g of the copolymer of Example 18, 0.20 g dicyclohexyl-18-crown-6, 0.16 g of the dipotassium salt of bisphenol A, 0.20 g MgO and 0.52 g SAF carbon black. The milled material was degassed at 50° in a vacuum oven and cured at 200° under $N_2$ for three days. Post curing was done at 300° for one day under nitrogen. This gave a solid with a very slight amount of flow on standing at room temperature. Differential scanning calorimetry showed a Tg of −58°.

EXAMPLE 20

Copolymerization of Perfluoro(9,10-epoxy-5-methyl-4,7-dioxadecanenitrile) with Hexafluoropropylene Oxide

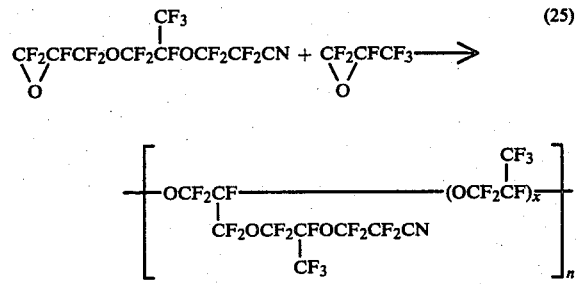

Following the procedure for HFPO copolymerization (Example 11), 7 g of perfluoro(9,10-epoxy-5-methyl-4,7-dioxadecanenitrile) prepared as in Example 8 and 312 g of HFPO were copolymerized at −33° to −35° over a period of 76.4 hr. IR showed a molecular weight of 28,000 and a nitrile comonomer content of 2.7% by weight. X in formula is approximately 99.

EXAMPLE 21

Copolymerization of Perfluoro(1,2-epoxy-7-phenoxy-4-oxaheptane) with Hexafluoropropylene Oxide

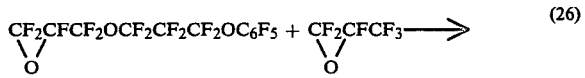
(26)

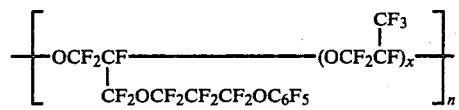

Following the procedure for HFPO copolymerization (Example 12), 5.84 g of the phenoxy monomer prepared as in Example 10 and 192.59 g of HFPO were copolymerized over a period of 51 h at −33° to −35°. The molecular weight by IR was 15,000. x in the the formula is approximately 99.

EXAMPLE 22

Post-Polymerization Conversion of Acid Fluoride to Amide

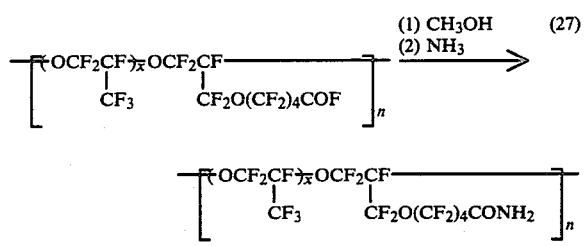
(27)

A mixture of 10.0 g of the copolymer prepared in Example 15, 20 ml of $CFCl_2CF_2Cl$ (1,1,2-trichlorotrifluoroethane), 20 ml of methanol and 5.0 g of sodium fluoride was stirred at 25° for 2 days. The resulting mixture contained copolymers wherein —COF groups were replaced with —$CO_2CH_3$ groups. The mixture was stirred further at 25° while ammonia was bubbled in slowly to saturation, and the mixture was stirred for 2 days with occasional addition of more ammonia. Volatiles were then removed under vacuum, the residue was stirred with 25 ml of $CFCl_2CF_2Cl$, and the mixture was filtered. Evaporation of the filtrate afforded 10.2 g of amidated polymer. IR (neat): 2.84 (NH) and 5.74µ (C=O).

The above interconversions may equally well be carried out using starting copolymers of this invention which contain —COCl, —$CO_2H$ or —$CO_2R^4$ groups in place of —COF. When a —$CO_2R^4$ functional polymer is employed, the methanolysis step is unnecessary; methanolysis is optional with polymers containing acyl halide functions.

EXAMPLE 23

Post-Polymerization Conversion of Sulfonyl Fluoride to Sulfonate

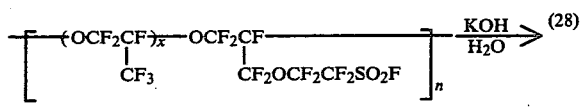
(28)

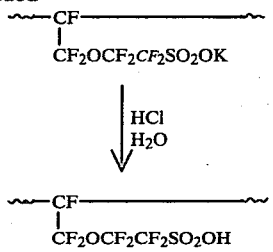

50.0 g (0.0255 equivalents) of the copolymer prepared in Example 11 was stirred with a solution of 40 g (0.6 mol) of 85% KOH pellets in 160 ml of water for 2 h at 90°. The taffy-like potassium salt of the sulfonated polymer solidified on standing overnight. Analysis by IR showed the sulfonyl fluoride groups to be completely reacted. The solid was broken up and filtered off. The filter cake was stirred with 200 ml of 10 N HCL at 25°, then with 200 ml and 400 ml of 10 N HCL at 95°, during which time it was converted to a soft semisolid. The resulting sulfonated polymer was exceptionally hydrophilic and weighed 100 g after drying under vacuum.

We claim:

1. Perfluoroglycidyl ethers of the formula

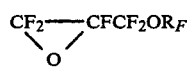

wherein $R_F$ is:

(i)

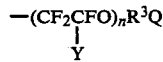

wherein $R^1$ is a carbon-carbon bond or a linear or branched perfluoroalkylene group of 1 to 12 carbon atoms; Q is —$SO_2F$, —COF, —F, —Cl, —Br, —I, —CN, —$CO_2H$, —$OC_6F_5$, or —$CO_2R^4$ where $R^4$ is —$CH_3$ or —$C_2H_5$; Y and Y' are —F or —$CF_3$, provided that only one of Y and Y' can be —$CF_3$; or (ii) —$CF(R^2)_2$ wherein $R^2$ is —F, —$CF_2Cl$, —$CF_2CN$, —$CF_2COF$, —$CF_2CO_2H$, —$CF_2OCF(CF_3)_2$ or —$CF_2CO_2R^4$ where $R^4$ is defined as above; or (iii)

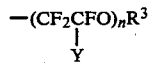

wherein $R^3$ is a linear or branched perfluoroalkylene group of carbon content such that the moiety —$(CF_2CFO)_nR^3$
|
Y does not exceed 15 carbon atoms; Y independently is —F or —$CF_3$; n is 1 to 4; and Q is as defined above; or (iv) —$C_6F_5$.

2. The perfluoroglycidyl ethers of claim 1 in which $R_F$ is —$CF_2R^1CF_2Q$ wherein Q is selected from the group consisting of —$SO_2F$, —$CO_2R^4$, —CN, —$OC_6F_5$, —Br, —I, and —COF.

3. The perfluoroglycidyl ethers of claim 1 in which $R_F$ is —$CF(R^2)_2$ where $R^2$ is —$CF_2CO_2R^4$, —$CF_2COF$ or —$CF_2CN$; and $R^4$ is —$CH_3$.

4. The perfluoroglycidyl ether of claim 1 wherein $R_F$ is —$C_6F_5$.

* * * * *